US005854233A

United States Patent [19]
McLean

[11] Patent Number: 5,854,233
[45] Date of Patent: Dec. 29, 1998

[54] METHOD OF TREATING LIVER DISEASE AND LIKE INDICATIONS WITH VASODILATING AGENTS

[75] Inventor: Allan Joseph McLean, South Melbourne, Australia

[73] Assignee: Pharmacy and Therapeutic Advisory Consultancy Ltd., London, England

[21] Appl. No.: 667,147

[22] Filed: Jun. 20, 1996

Related U.S. Application Data

[63] Continuation-in-part of PCT/AU94/00525, Sep. 15, 1994, and a continuation-in-part of Ser. No. 612,286, Mar. 7, 1996, abandoned.

[30] Foreign Application Priority Data

Sep. 8, 1993 [AU] Australia .............................. PM 11104

[51] Int. Cl.$^6$ .................................................. A61K 51/55
[52] U.S. Cl. ........................ 514/211; 514/213; 540/491; 540/523
[58] Field of Search .................................. 514/211, 213; 540/491, 523

[56] References Cited

U.S. PATENT DOCUMENTS

| 4,902,684 | 2/1990 | Floyd et al. ............................. | 514/211 |
| 5,569,678 | 10/1996 | Lee ......................................... | 514/654 |

FOREIGN PATENT DOCUMENTS

| 44849/68 | 10/1968 | Australia . |
| 16326/92 | 5/1992 | Australia . |
| WO92/04008 | 3/1992 | WIPO . |
| WO95/07080 | 3/1995 | WIPO . |

OTHER PUBLICATIONS

Marteau et al., "Effect of Vasodilators on Hepatice Microcirculation: A Study of the Inhibition of Norepinephrine–Induced Vasoconstriction in the Isolated Perfused Rat Liver", Hepatology, vol. 8, No. 2, 1988, pp. 228–231, XP000673345.
Marteau et al., "Effect of Vasodilators on Hepatic Microcirculation in Cirrhosis: A Study in the Isolated Perfused Rat Liver", Hepatology, Vo. 9, No. 6, pp. 820–823, XP000673346 (1989).
Hierlinger, "Chronic Verapamil Administration Improves Liver Function and Diffusional Exchange in a Rat Model of Liver of Liver Cirrhosis", J. Hepatol., No. Suppl. 2, 1985, p. S253, XP0002030787.
Ramanao et al., "Alterazione degli enzimi epactici in corso di terapia con diltiazem", G. Ital. Cardiol., vol. 17, No. 2, 1987, pp. 149–150, XP000673314.
Navasa et al., "Effects of Verapamil on Hepatic and Systemic Hemodynamis and Liver Function in Patients with Cirrhosis and Portal Hypertension", Hepatology, vol. 8, No. 4, 1988, pp. 850–854, XP000673312.
Merkel et al., "Lack of effect of verapamil and isosorbide dinitrate on the hepatic clearance of indocyanine green in cirrhosis", Br. J. Clin. Pharmacol., vol. 30, No. 2, 1990, pp. 221–228, XP000673273.

Gasic et al., "Comparative effects of verapamil, taipamil, diltiazem and nifedipine on systemic and splanchnic hemodynamis in man", Int. J. Clin. Pharmacol., Ther. Toxicol., vol. 25, No. 9, 1987, pp. 498–503, XP000673344.
MacMathuna et al., "Vasopressin–nifedipine: a favourable haemodynamic interaction in cirrhosis and portal hypertension", Eur. J. Gastroenterol. Hepatol, vol. 5, No. 10, 1993, pp. 853–857, XP000673271.
Extract from The Merck Manual of Diagnosis and Therapy, 16th Edition; Merck Research Laboratories; Ch. 286, pp. 2670–2671 (1989).
Rosman "Viral hepatitis anc alcoholism" Alcohol, health & Research World, v.16, p. 48, 1992.
Dorland's Medical dictionary, p. 1979, 1992.
Mountcastle "Medical physiology" p. 239, 1968.
Bhathal et al. "Reduction of the increased portal vascular resistance of the isodlated perfused cirrhotic rat liver by vasodilator" CA 103:189411, 1985.
Wyngaarden "Textbook of medicine" Sanders Co. pp. 779, 786, 787, 1983.
Hubert J. Stein et al., "Effect of Verpamil on Hepatic Ischemia/Reperfusion Injury", The American Journal of Surgery, vol. 165, Jan. 1993, pp. 96–100.
Decai Liang et al., "Protective Effects of the Calcium Antagonists Diltiazem and TA3090 Against Hepatic Injury Due to Hypoxia", Biochemical Pharmacology, vol. 44, No. 11, pp. 2207–2211, 1992.
David Le Courteur et al., "Aging and the Response of the Isolated Perfused Rat Liver to Vasoactive Drugs", Biochemical Pharmacology, vol. 43, No. 4, pp. 913–915, 1992.
Nobuyuki Ogawa et al., "Comparison of KRN2391 with Nicorandil and Nifedipine on Canine Coronary Blood Flow: Antagonims by Glibemclamide", Journal of Cardiovascular Pharmacology, pp. 11–17, 1992.
Stephen Cheng, et al., "Verapamil Improves Rat Hepatic Preservation with UW Solution", Journal of Surgical Research 50, pp. 560–564, 1991.
William G. Reiss et al., "The Effects of Oral Nifedipine on Hepatic Blood Flow in Humans", Clinical Pharmacology and Therapeutics, vol. 50, pp. 379–384, Oct. 1991.
Jiri Heller et al., "The effect of two different calcium antagonists on the glomerular haemodynamics in the dog", European Journal of Physiology (Berlin), vol. 415, No. 6, pp. 751–755, 1990.

(List continued on next page.)

Primary Examiner—Ceila Chang
Attorney, Agent, or Firm—McDermott, Will & Emery

[57] ABSTRACT

Liver diseases, such as cirrhosis of the liver, toxic and medicamentary liver damage, a liver-parenchymic disorder or hepatitis, are treated by administering to a human or animal subject in need thereof a therapeutically active or prophylactically effective low dose amount of a vasodilating agent which selectively increases the supply of oxygenated blood to the liver by increasing hepatic arterial inflow. Suitable vasodilating agents include calcium blockers, such as a benzothiazepine derivative, nifedipine, felodipine or verapamil.

13 Claims, 10 Drawing Sheets

OTHER PUBLICATIONS

Denis B. Buxton, "*Potentiation of the glycogenolytic and haemodynamic actions of adenosine in the perfused rat liver by verapamil*", European Journal of Pharmacology, 146 pp. 121–127, 1988.

J. Reichene et al., "*Verapamil Favorably Influences Hepatic Microvascular Exchange and Functions in Rats with Cirrhosis of the Liver*", The American Society for Clinical Investigation, Inc., vol. 78, Aug. 1986, pp. 448–455.

P.A. Meredith et al., "*Verapamil Pharmacokeinetics and Apparent Hepatic and Renal Blood Flow*", British Journal of Clinical Pharmacology, vol. 20, No. 2, 1985, pp. 101–106.

Patent Abstract of Japan JP 5–59028, Yoshiaki Oshida, "*Benzothiazepine Derivative, its Salt and Medicine Composition Containing the Same*", Sep. 3, 1993.

Patent Abstract of Japan JP 56–68619, Yamanouchi Seiyaku, "*Nifedipine–Containing Solid Composition*", 9 Jun. 1981.

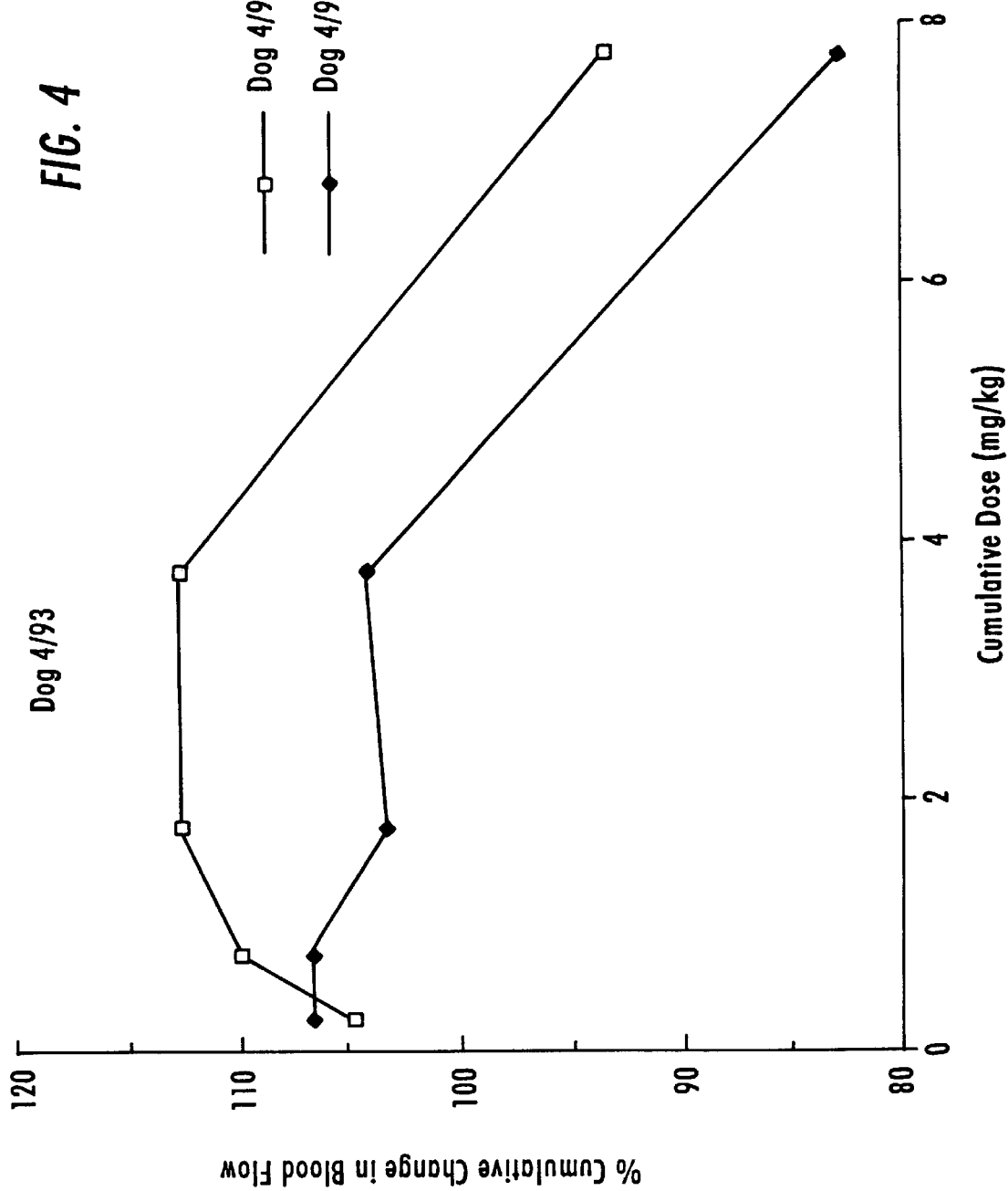

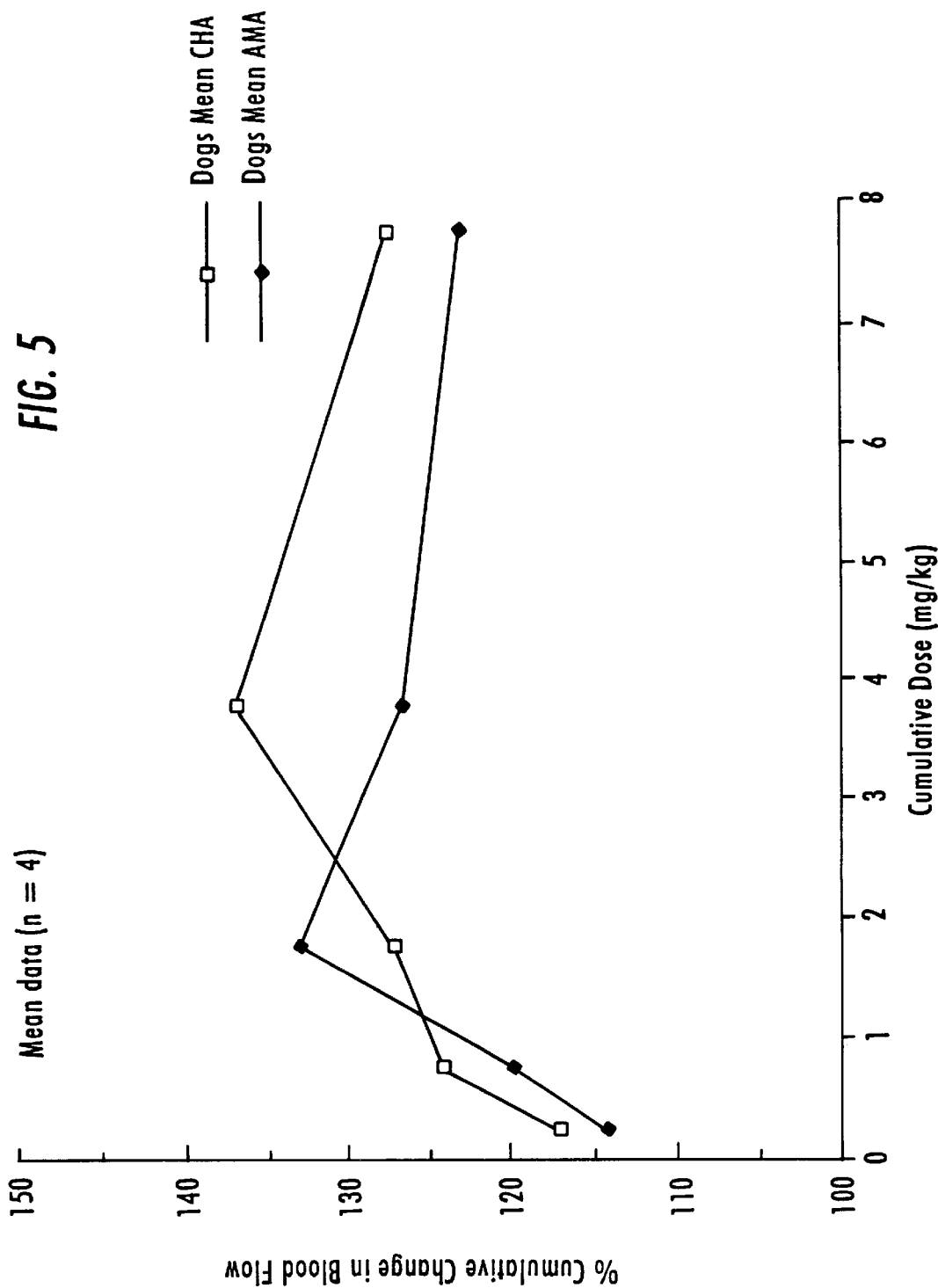

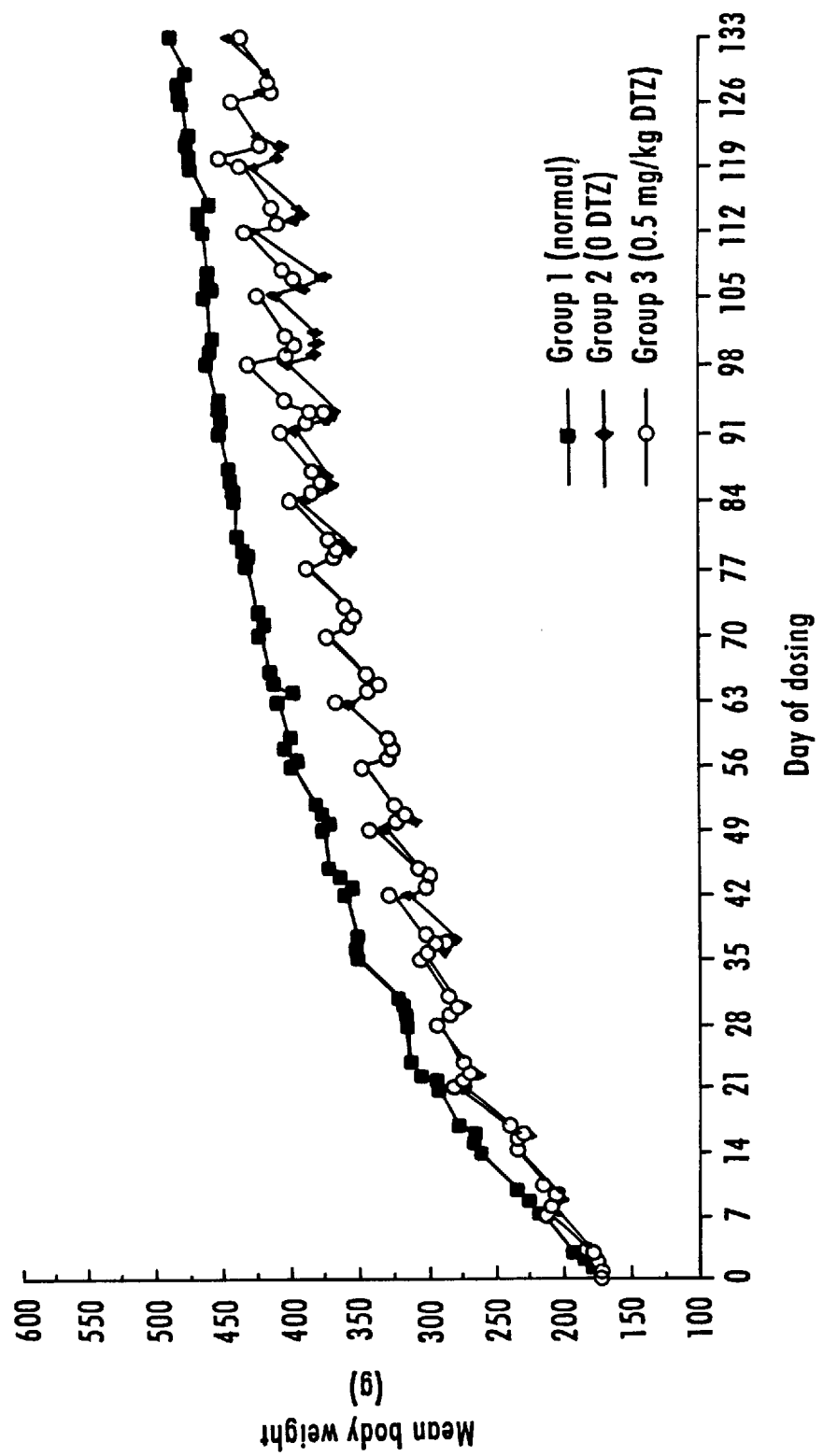

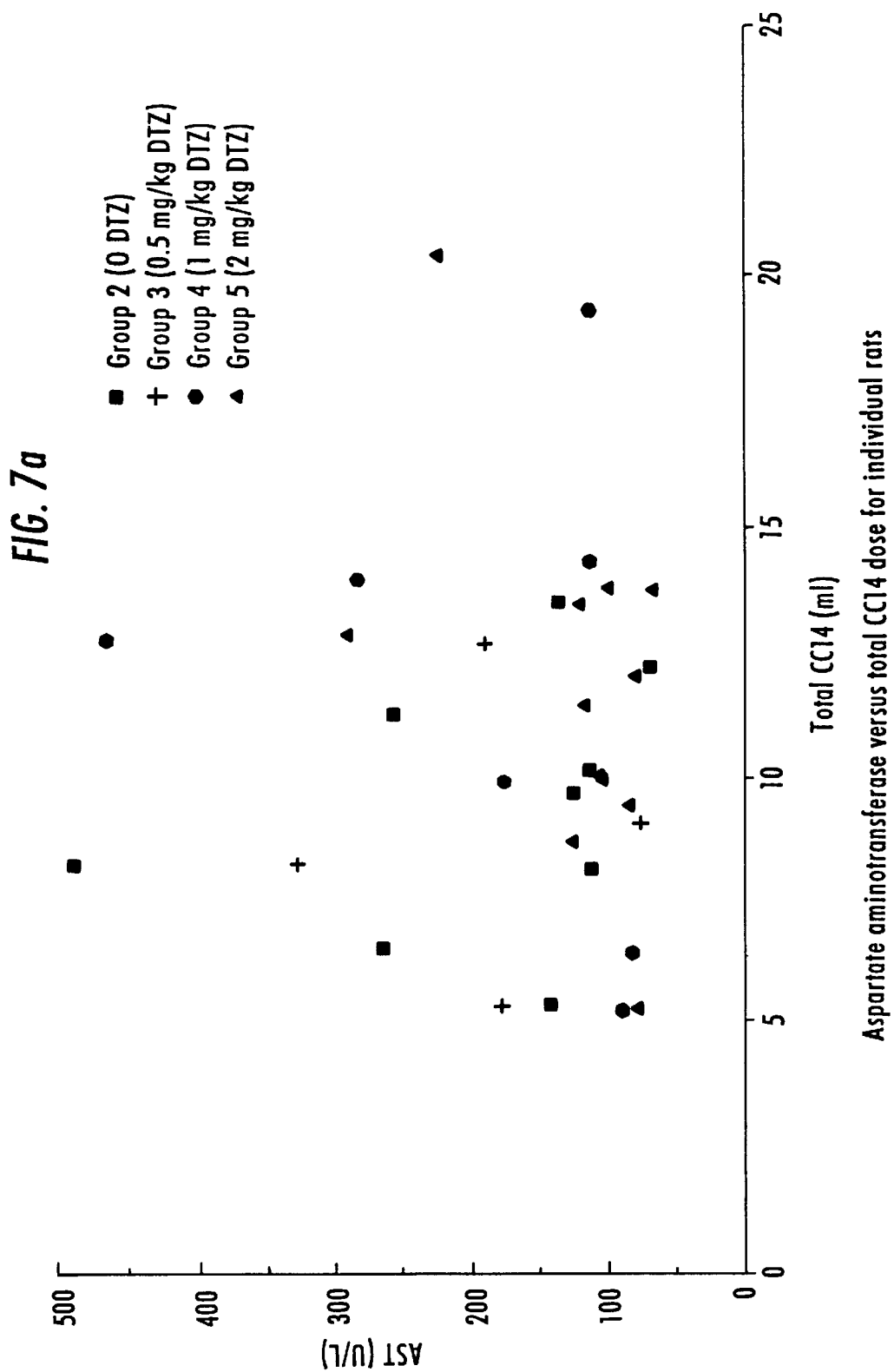

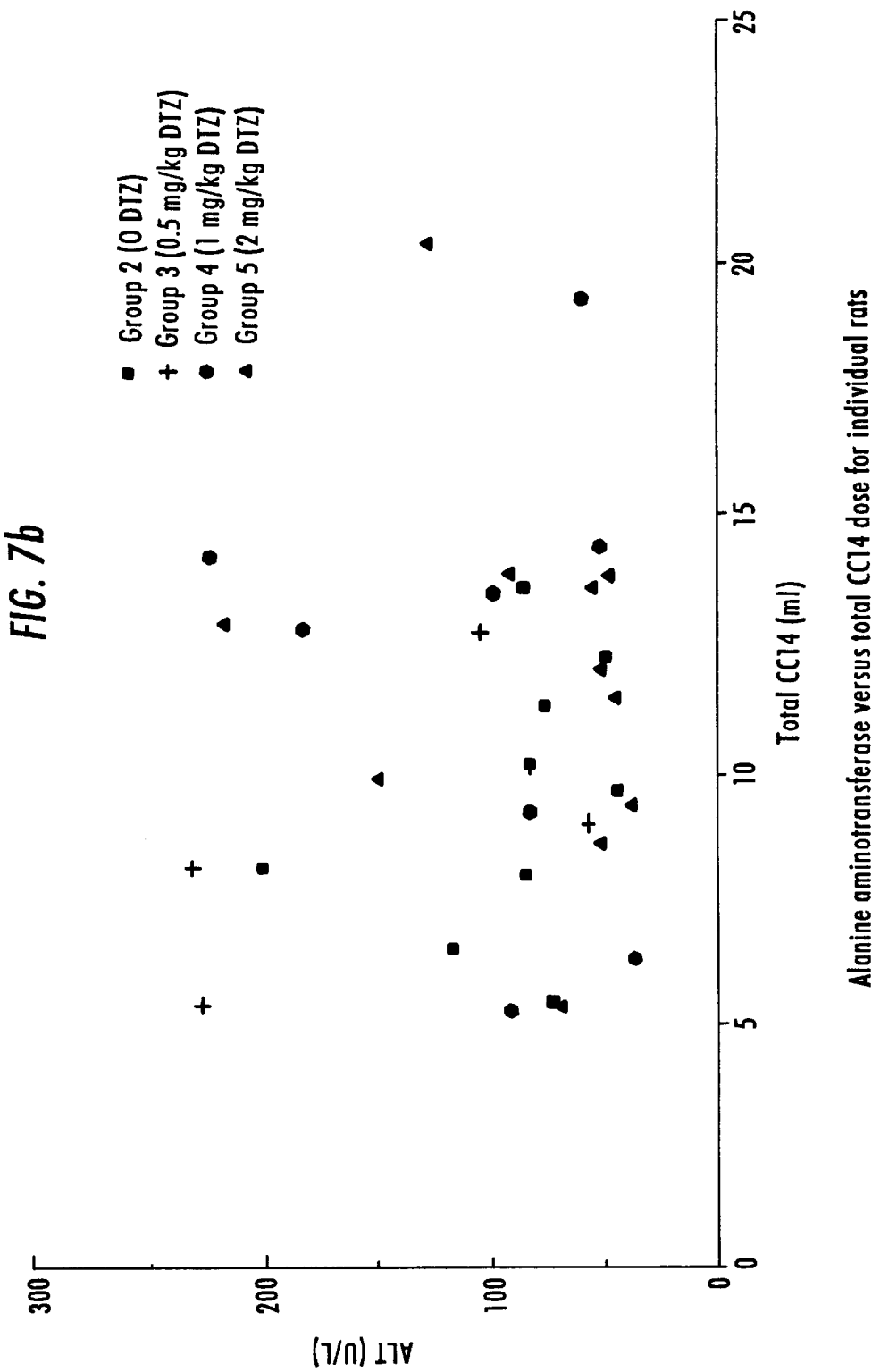

METHOD OF TREATING LIVER DISEASE AND LIKE INDICATIONS WITH VASODILATING AGENTS

TECHNICAL FIELD

This is a continuation-in-part of PCT International Application Serial No. PCT/AU94/00525, filed Sep. 5, 1994, and a continuation-in-part of U.S. patent application Ser. No. 08/612,286, filed Mar. 7, 1996, now abandoned.

The present invention relates to a method for the treatment of liver disease. The invention also relates to compositions suitable for the use in the treatment of liver disease.

Diltiazem is the generic name given to the active component of a composition that is primarily used for the treatment of heart disease. Specifically it is known as 3-acetoxy-5-(2- (dimethylaminoethyl)-2,3-dihydro-2-(4-methoxy phenyl)-1,5-benzothiazepine-4)5H-one. This compound is the active ingredient in the heart treatment drug Cardizem. Cardizem has particular efficacy in the treatment of ischaemic heart disease including angina pectoris and hypertension.

Diltiazem is a member of a broad class of benzothiazepine derivatives that are the subject of Australian Patent 426146. The class of compounds are referred to in that specification as having particular utility as anti-depressants, tranquilizers and coronary vasodilators.

Diltiazem primarily acts as a calcium channel antagonist (a calcium blocker); calcium being involved in several biological process in the human body including vasoconstriction and vasodilation. Calcium blockers interfere with the transport of calcium through the cell membrane, thus reducing the contraction of vascular smooth muscle and causing the arteries to dilate The discovery of calcium blockers constituted a major advance in cardiovascular treatment.

Diltiazem contributed significantly to this advance. Generally, during cardiovascular treatment using Diltiazem, a patient in need thereof is administered the drug in doses of from 180 mg to 360 mg per day.

The liver is a large gland situated in the upper part of the abdomen on the right side. Its domed upper surface fits closely against the inferior surface of the right diaphragm It has a double blood supply from the hepatic artery (oxygenated arterial blood) and the portal vein (deoxygenated venous blood carrying substances absorbed from the stomach, small intestine and large intestine). It comprises thousands of minute lobules (lobuli hepatis), the functional units of the liver. Its manifold functions include the storage and filtration of blood, the secretion of bile, the excretion of bilirubin and other substances formed elsewhere in the body, and numerous metabolic functions, including the conversion of sugars into glycogen, which it stores. It is essential to life and accordingly liver disfunction is debilitating and life threatening.

Prior art treatments of liver disease have included use of a number of drugs. For example, choline has been administered as an adjunct to the dietary O treatment of fatty acid infiltration and early cirrhosis of the liver. Methionine has a lipotropic action similar to choline. It has also been used as an adjunct in the treatment of liver diseases in patients unable to take an adequate diet, though there is evidence that in cases of severe liver damage large doses of methionine may aggravate the toxaemia. Litrison is a composition of methionine, choline, vitamins of the B complex and Vitamin E. It has been used for the treatment of hepatic parenchymal degenerative changes and to maintain the function of the liver. Neurogem is a composition of high potency essential Vitamin B-complex and Vitamin C which has been used for supplementary or maintenance therapy. Finally, Ripason is a protein-free total extract from livers of healthy animals. It has been used to treat chronic hepatitis, cirrhosis, medicamentous liver damage and liver parenchyma disorders.

The treatment of liver disease, however, has been an ongoing difficulty in the prior art and none of the drugs used have proved to be particularly effective. In particular, none of these agents reverses the relative hypoxia, or oxygen lack, which appears to contribute to the pathology and progression of chronic liver disease. Accordingly, liver disease continues to be a life-threatening disease and ultimately may require surgery or even transplants in some cases.

Accordingly, it is an object of the present invention to overcome, or at least alleviate, one of more of the difficulties or deficiencies related to the prior art.

Accordingly, in a first aspect of the present invention, there is provided a method for the treatment of liver disease and like indications, which method includes administering to a human or animal subject in need thereof a therapeutically or prophylactically effective amount of a vasodilating agent which selectively increases the supply of oxygenated blood to the liver.

The vasodilating agent may include a calcium blocker, e.g. a thiazepine derivative, preferably a benzothiazepine derivative, nifedipine, felodipine or verapamil. Other vasodilators may be used indirectly.

The method of treatment may be utilized in the treatment of various diseases of the liver such as cirrhosis of a liver, toxic and medicamentary liver damage or liver parenchymic disorders and related diseases such as hepatitis including chronic active hepatitis.

The method of treatment may be directional in that significantly lower doses may be used then are normally administered in the treatment of heart disease or like indications.

BRIEF DESCRIPTION OF THE DRAWINGS

Reference is now made to the drawings which accompany the application wherein:

FIGS. 1, 2, 3, 4, and 5 are graphs of the results shown in Tables 2a and b;

FIGS. 6a, 6b, and 6c are graphs which show body weight profiles during DTZ administration of the results of Example 3; and FIGS. 7a and 7b are plots of AST and ALT enzyme release vs. Total Body load of $CCl_4$ of data from Table 3.

Figure 1:
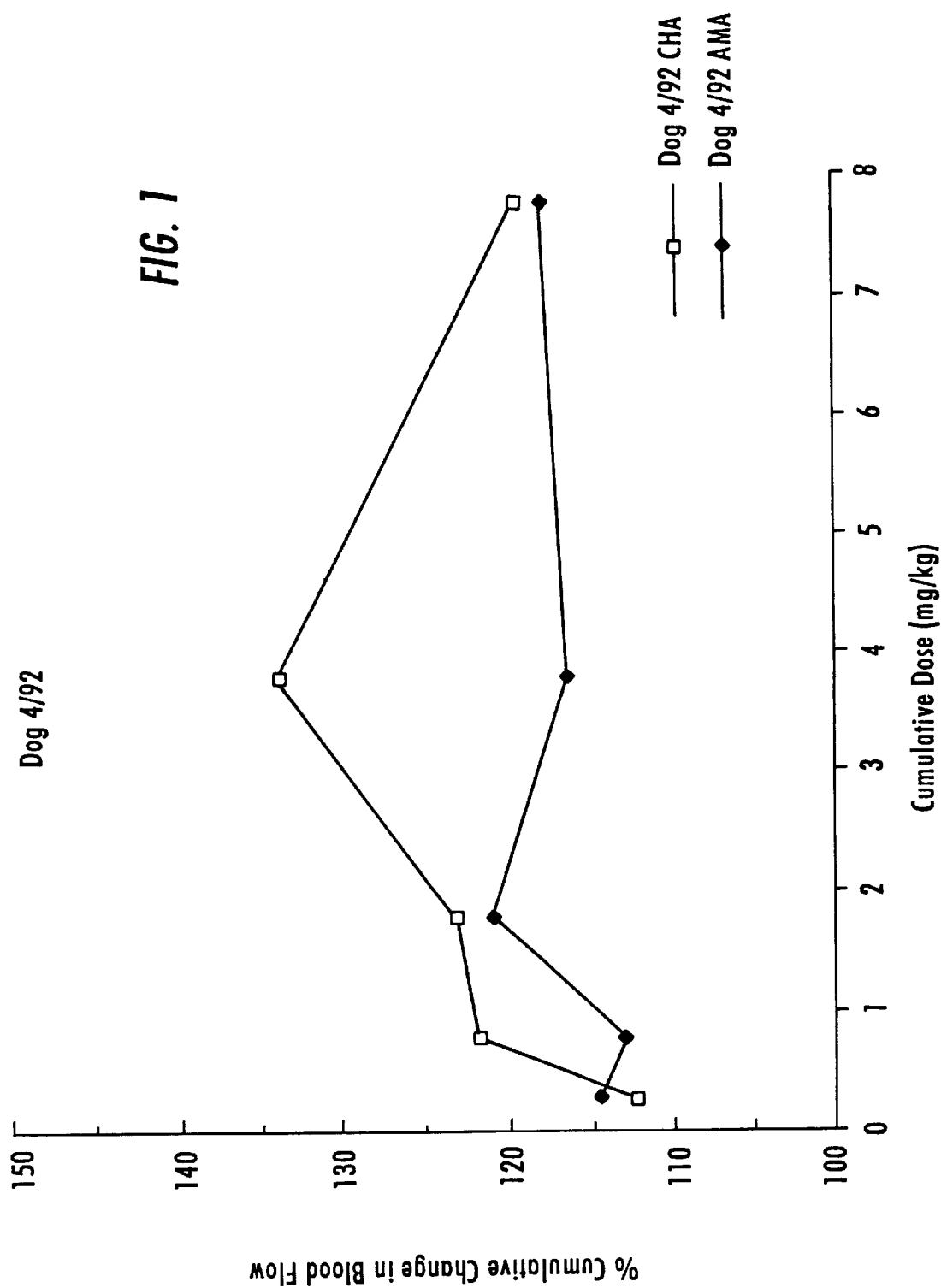
Figure 2:
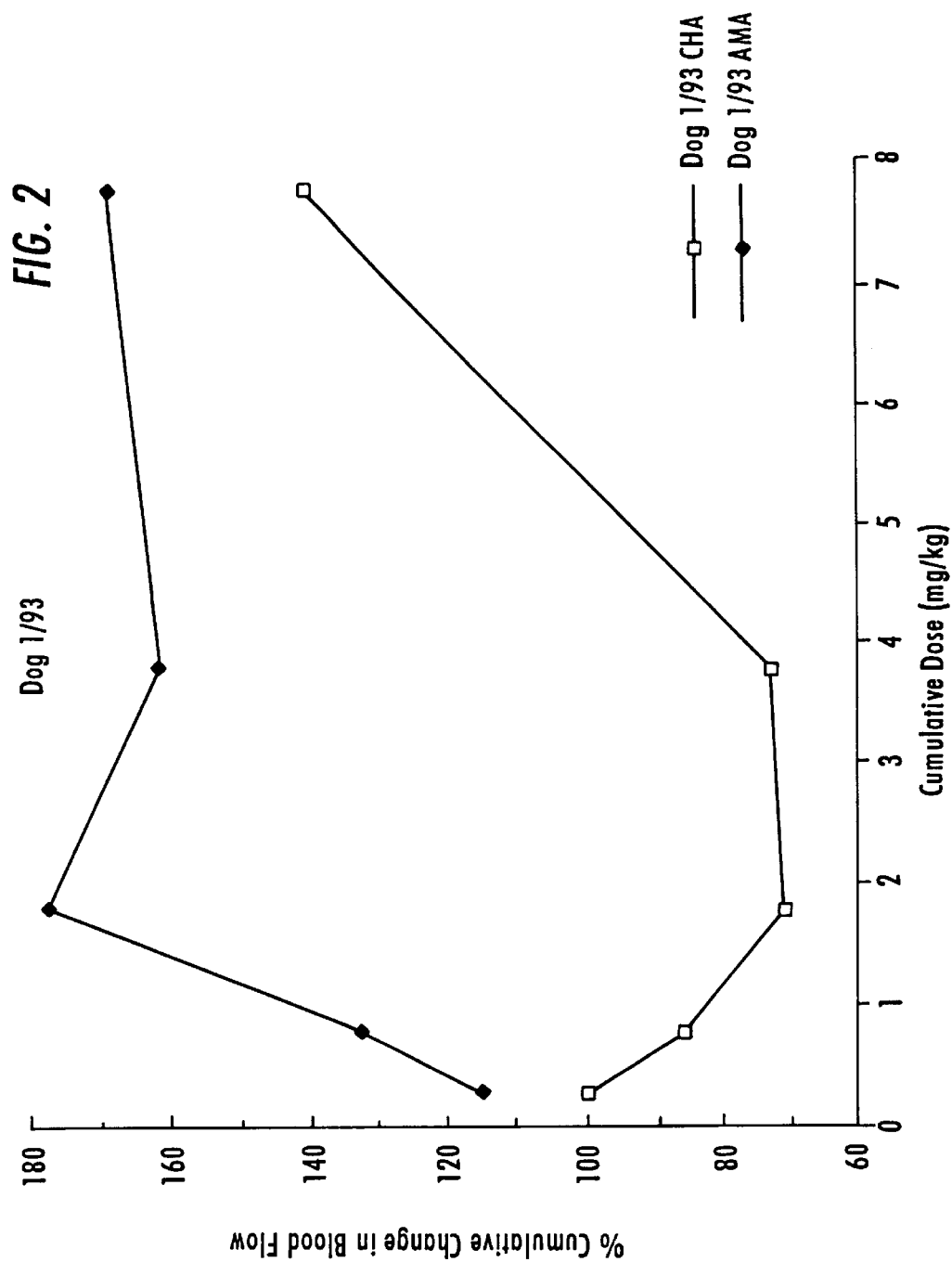
Figure 3:
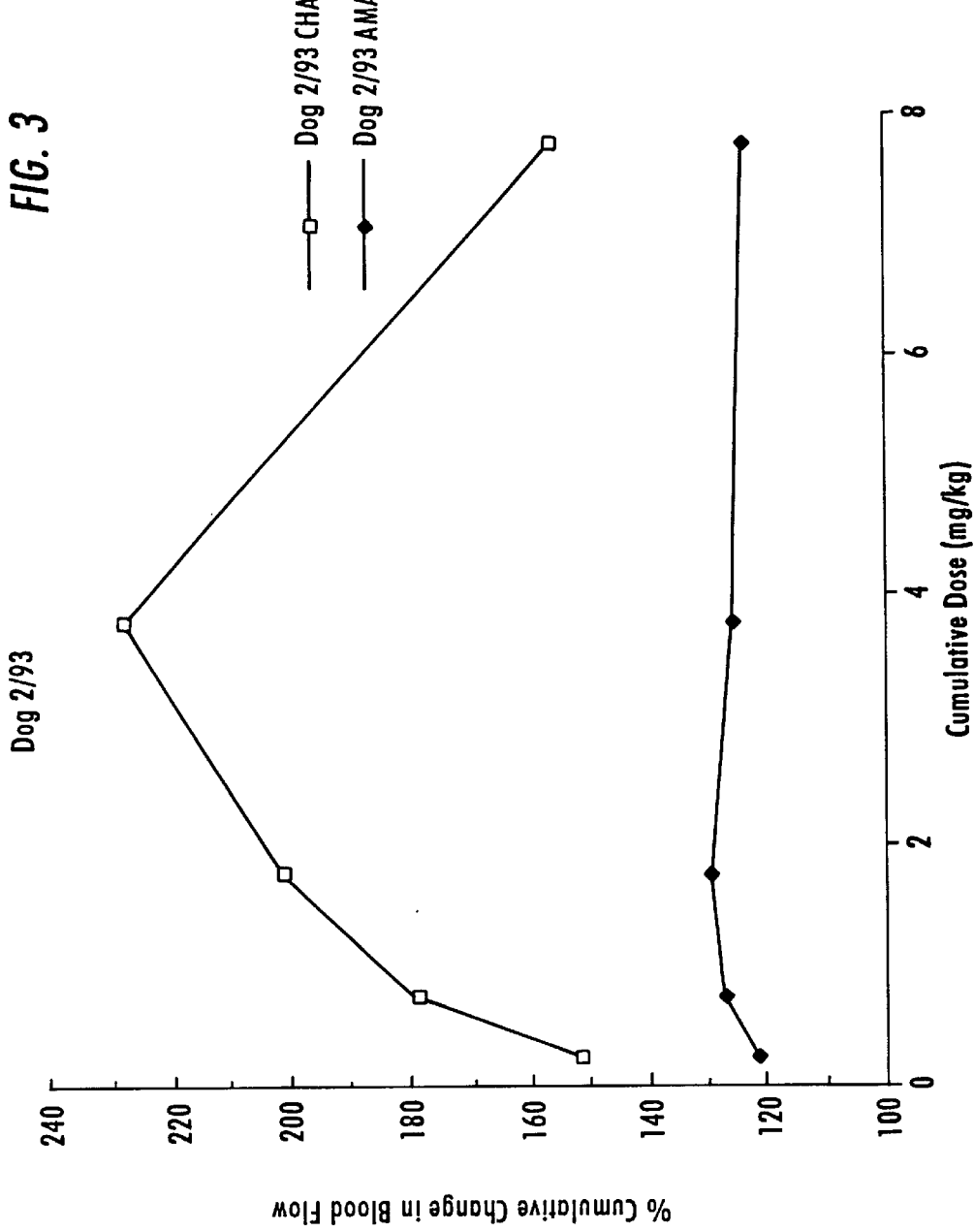

Whilst we do not wish to be restricted by theory, it is believed that the class of vasodilating agents known as calcium blockers are effective in the treatment of liver disease as they are selectively able to increase the oxygen content to the liver. In particular, it is believed that calcium blockers are effective in the treatment of liver disease as they are selectively able to dilate the hepatic artery. An increase in oxygen level may alleviate the progress of liver disease, since liver performance generally increases with an increase in the oxygen concentration. Common liver diseases, such as chronic hepatitis or cirrhosis of the liver, share as a pathological feature a low concentration of oxygen in the liver.

Accordingly in a further aspect of the present invention there is provided a method for the treatment of liver disease which method includes administering to a human or animal subject in need thereof a therapeutically or prophylactically effective amount of a benzothiazepine derivative of the formula:

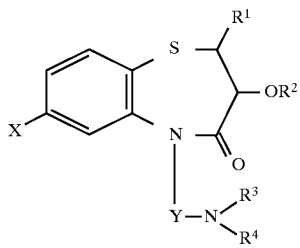

wherein $R^1$ is a phenyl group substituted or not with 1 to 3 lower alkyl groups, lower alkoxy groups or halogen atoms, $R^2$ is a hydrogen atom or a lower alkanoyl group, $R^3$ and $R^4$ are each a lower alkyl group and may be the same or different, X is a hydrogen atom or a halogen atom and Y is an alkylene group of 2 or 3 carbon atoms, or its non-toxic acid-addition salt.

Preferably $R^1$ is 4-lower alkoxyphenyl, $R^2$ is lower is alkanoyl, $R^3$ and $R^4$ are each lower alkyl, X is hydrogen and Y is ethylene. More preferably $R^1$ is 4-methoxyphenyl, $R^2$ is acetyl and $R^3$ and $R^4$ are each methyl. Still more preferably, the benzothiazepine derivative is 3-acetoxy-5-(2-(dimethylaminoethyl) -2,3-dihydro-2- (4-methoxy phenyl)-1,5-benzothiazepine-4) 5H-one.

The benzothiazepine derivative may be converted into its acid-addition salts by treatment with an organic or inorganic acid (e.g. acetic acid, oxalic acid, malonic acid, tartaric acid, malic acid, citric acid, lactic acid, gluconic acid, aspartic acid, hydrochloric acid, hydrobromic acid, sulfuric acid, nitric acid, ID perchloric acid, etc.) in a suitable solvent (e.g. water, methanol, ethanol, etc.). It has been found that the use of such benzothiazepine derivatives is effective in increasing the hepatic arterial blood flow to the liver. Such benzothiazepine derivatives may be effective in the treatment of liver disease in significantly lower doses than is normally administered in the treatment of heart diseases. Significantly lower mean doses which will have no significant effect on heart or peripheral circulation.

In a further preferred aspect of the present invention there is provided a method of treating liver disease which method includes administering to a patient in need thereof a low dose, e.g., approximately 2.5 mg to 100 mg per day, more preferably approximately 2.5 mg to 60 mg/day, and even more preferably 10 mg to 60 mg/day of diltiazem or its non-toxic acid-addition salt. Experimental studies in mice to date have indicated effective doses of approximately 1.0 to 2.0 mg/kg/day. However, it is common for human doses to be lower than for animals including rodents. A dose of approximately 2.5 mg to 30 mg, preferably 10 mg to 30 mg, per day may be used for patients with higher grades of liver disease. A dosage of approximately 30 mg to 100 mg, preferably 30 mg to 60 mg per day, may be used for patients with lower grades of liver disease.

According to a further aspect of the present invention there is provided a pharmaceutical composition suitable for the treatment of liver disease and like indications which composition includes a therapeutically or prophylactically effective amount of a vasodilating agent which selectively increases the supply of oxygenated blood to the liver and a pharmaceutically acceptable diluent or carrier therefor.

The vasodilating agent may include a calcium blocker, e.g. a thiazepine derivative, preferably a benzothiazepine derivative, nifedipine, felodipine or verapamil. Other vasodilators may be used indirectly.

The pharmaceutical composition may be utilized in the treatment of various diseases of the liver such as cirrhosis of a liver, toxic and medicamentary liver damage or liver parenchymic disorders and related diseases such as I0 hepatitis including chromic active hepatitis.

In a further preferred aspect of the present invention there is provided a pharmaceutical composition suitable for the treatment of liver disease and like indications which composition includes a therapeutically or prophylactically effective amount of a benzothiazepine derivative of the formula:

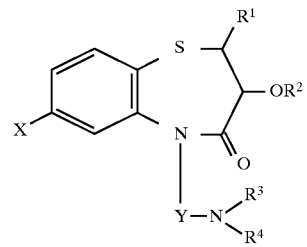

wherein $R^1$ is a phenyl group substituted or not with 1 to 3 lower alkyl groups, lower alkoxy groups or halogen atoms, $R^2$ is a hydrogen atom or a lower alkanoyl group, $R^3$ and $R^4$ are each a lower alkyl group and may be the same or different, X is a hydrogen atom or a halogen atom and Y is an alkylene group of 2 or 3 carbon atoms, or its non-toxic acid-addition salt; and a pharmaceutically acceptable diluent or carrier therefor.

Preferably $R^1$ is 4-lowe alkoxyphenyl, $R^2$ is lower alkanoyl, $R^3$ and $R^4$ are each lower alkyl, X is hydrogen and Y is ethylene. More preferably $R^1$ is 4 -methoxyphenyl, $R^2$ is acetyl and $R^3$ and $R^4$ are each methyl. Still more preferably, the benzothiazepine derivative is 3-acetoxy-5-(2-(dimethylaminoethyl)2,3-dihydro-2-(4-methoxy phenyl)-1,5-benzothiazepine-4)5H-one.

In a further preferred aspect of the present invention there is provided a pharmaceutical composition suitable for the treatment of liver disease and like indications which composition includes approximately 2.5 mg to 60 mg, preferably 10 mg to 60 mg per day of diltiazem or its non-toxic acid-addition salt, and a pharmaceutically acceptable diluent or carrier therefor. A dosage at the low level of the range may be used in patients with higher grades of liver disease.

The pharmaceutically acceptable diluent or carrier may be of any suitable type. The pharmaceutically acceptable diluent or carrier may be a pharmaceutical organic or inorganic carrier material suitable for enteral, parenteral or transdermal applications.

Preferably the composition is formulated so as to allow suitable administration to the patient. Such administration may be by any suitable means such as oral, subcutaneous, intravenous or transcutaneous. Preferably administration is by oral route as the active ingredient is able to reach the liver directly, that is through the portal vein.

Oral administration by the use of tablets, capsules, powders or in liquid form such as suspensions, solutions, emulsions or syrups is particularly advantageous. When formed into tablets, conventional excipients (e.g. sodium citrate, lactose, microcrystalline cellulose, starch, etc.), lubricating agents (e.g. anhydrous silicic acid, hydrozed castor oil, magnesium stearate, sodium lauryl sulfate, talc, etc.) and binding agents (e.g. starch paste glucose, lactose, gum acacia, gelatin, mannitol, magnesium trisilicate, talc, etc.) can be used.

When administered as liquids, conventional liquid carriers can be employed. In the case of solid preparations, each unit dosage form of the active ingredient can contain from about 5 to about 95% of the same by weight of the entire composition with the remainder comprising conventional pharmaceutical carriers. When the therapeutic agent is used as aqueous solution, i.e., injection, the solution may contain about 0.05 to about 0.5% of the same by weight of the entire solution.

Preferably the composition may be of the sustained release type, for example to allow for a once-daily administration. The sustained release composition may be suitable for oral or transdermal administration. A suitable slow release formulation may be achieved for example when the active ingredient is bound to a suitable polymer. A once daily composition is able to supply sufficient quantity of active ingredient to the patient and may avoid the possibility of toxic shock where multi-doses are given on a daily basis to patients suffering liver disease.

The present invention will now be more fully described with reference to the accompanying examples. It should be understood, however, that the description following is illustrative only and should not be taken in any way as a restriction on the generality of the invention described above.

EXAMPLE 1

Aim

A pilot study was undertaken to examine the effect on hepatic artery and mesenteric artery flow in anaesthetized dogs when exposed to cumulative doses of diltiazem.

Methods

Preparation:

Greyhounds were used in this pilot study. All dogs were present in the animal house for <1 week prior to surgery, and all were deemed clinically sound. Dogs were given 15 minutes of exercise prior to arriving at the theater. On arrival, they were clipped on the abdomen, forelimbs and hindquarters, and anaesthesia was induced withum pentobarbitone (Nembutal for injectionT) given intravenously to effect. Subjects were intubated and connected to a respirator. Table heating was used to maintain body temperature. An initial infusion of 1 liter of Hartmann's solution was given throughout the surgical procedure, with bicarbonate being administered as required according to blood gas estimation.

The abdomen was opened, and the gastro-duodenal branch of the common hepatic artery was located and ligated Electromagnetic flow probes were placed on the common hepatic artery and the anterior mesentenc artery. A branch of the splenic vein was exposed and a catheter introduced and advanced into the portal vein. A catheter was also placed in the left hepatic vein using a purse string technique. An indwelling catheter was placed in a branch of the mesenteric vein, in close proximity to another catheter placed in the lumen of the jejunum. The abdomen was then closed and a catheter introduced into the femoral artery.

The subject was then covered with drapes, and the dogs circulation and temperature allowed to stabilize prier to the commencement of the experimental stage.

At the end of the study, the dogs were euthanased with sodium pentobarbitone.

Experimental Procedure:

Theophylline was used infused as a marker of liver extraction. A bolus was given (over 15 minutes) at a rate of 3.42 mg/min, then an infusion into the mesenteric vein at a rate of 11 mg/min. After 90 minutes stabilization, the first dose of diltiazem was given (0.25 mg/kg) into a jejunal lumen. Time was allowed for any changes in blood flow before the next dose was given. Effects on flow reached a plateau by 20 minutes, when the next dose was given. Cumulative doses were given, i.e. 0.25, 0.5, 1.0, 2.0, 4.0 mg/kg. Blood samples were taken throughout the procedure from the portal vein, posterior hepatic vein and arterial line at 20, 40, 60, 80, 90, 100, 110, 120, 130, 140, 150, 160, 170, 180 and 190 minutes, with zero time being the start of the theophylline infusion.

Results 6 dog Studies were performed, as per the summary in Table 1 below.

| Dog | Preparation | Experimental |
|---|---|---|
| Dog 3/92 | Surgery went well | No flow responses |
| Dog 4/92 | Surgery went well | Excellent flow responses to diltiazem |
| Dog 1/93 | Surgery went well | Flow response to diltiazem |
| Dog 2/93 | Surgery went well | Excellent flow responses to diltiazem |
| Dog 3/93 | Surgery unsuccessful | |
| Dog 4/93 | Surgery OK | Flow responses to diltiazem |

Statistical Observations

Mean flows were obtained in both the hepatic and mesenteric arteries for 10 to 20 minutes prior to diltiazem being given. This was taken as baseline flows, z and all measurements used this as baseline. Maximum flow responses were measured. The results are summarized in the tables 2a and b below and are presented diagrammatically in FIGS. 1–5.

TABLE 2a

Common Hepatic Artery

| Subject | +% CHA 0.25 mg/kg | +% CHA 0.5 mg/kg | +% CHA 1.0 mg/kg | +% CHA 2.0 mg/kg | +% CHA 4.0 mg/kg |
|---|---|---|---|---|---|
| 4/92 | 112.4 | 121.7 | 123.2 | 134.0 | 119.6 |
| 1/93 | 99.9 | 86.0 | 71.2 | 73.2 | 140.7 |
| 2/93 | 151.5 | 178.7 | 201.3 | 227.6 | 156.0 |
| 4/93 | 104.7 | 110.1 | 112.8 | 112.8 | 93.5 |
| MEAN | 117.1 ± 11.7 | 124.1 ± 19.7 | 127.1 ± 27.2 | 136.9 ± 32.8 | 127.5 ± 13.6 |

Two sets of experiments were performed. Both were conducted in dogs anaesthetized with barbiturates.

In the first series nitroglycerin was infused into either the portal vein (draining to the liver from the bowel) or to the femoral vein (systemic circulation). When nitroglycerin was given into the portal vein the blood flow through the hepatic artery, (i.e., a measure of liver blood flow and oxygenation) increased. By contrast when nitroglycerin was given systemically, hepatic blood flow reduced. It can be concluded that hepatic blood flow and liver oxygenation can both be augmented by drugs, but this cannot be achieved by systemic administration of nitroglycerin.

In the second series, diltiazem was administered by a gastric tube into the stomach—effectively orally. The level of blood flow through the hepatic artery increased by up to 50%, and this occurred at very small doses. Thus, increase in liver perfusion may be achieved by small doses of oral diltiazem and this will have a benefit on the diseased liver.

EXAMPLE 3

A third set of experiments was then undertaken in rats after the earlier studies in dogs had shown that low doses of diltiazem increased liver blood flow. The aim of the study was to induce liver disease by administration of carbon tetrachloride ($CCl_4$) and then test the hypothesis that low doses of diltiazem would improve the functional state of the liver.

Methods

Male Sprague Dawley rats were used in this study in which liver disease was induced after the method of Proctor and Chatamra (1982). Hepatic enzymes were first induced by addition of sodium phenobarbitone to the drinking water to a concentration of 350 mg/100 ml. All animals were given the phenobarbitone water for 10 weeks; no other water was available to the animals.

Animals randomized for induction of liver disease received $CCl_4$ added to maize oil, and administered orally through a stainless steel gavage tube during carbon dioxide stun. The $CCl_4$ was given for ten weeks as weekly doses commencing after two weeks of enzyme induction with phenobarbitone sodium. The starting dose of $CCl_4$ was 0.5 ml but the dose was then adjusted according to protocol to achieve a weight loss of 6 to 9% over the 3 days after each dose, with weight gain by day 7. Previous studies have shown that over a period of ten weeks, this regimen will produce liver disease with ascites, splenomegaly,reduction of plasma albumin, increase of plasma alanine transaminase, and the histological features of severe liver disease.

For the assessment of the effects of diltiazem, animals were separated into five groups each of 8 rats. Group 1 (normal) received phenobarbitone in the drinking water but no $CCl_4$ or diltiazem. Group 2 (control) received $CCl_4$ but no diltiazem. Groups 3, 4 and 5 received respectively 0.5, 1.0 and 2.0 mg/kg per day of diltiazem added to the drinking water.

The animals were weighed daily for the four days after each dose of $CCl_4$, and sacrificed after 12 weeks, that is, after 10 weeks of $CCl_4$+/− diltiazem, or at the equivalent time in normal animals. At autopsy, the weights of the livers and spleens were recorded, the presence of ascites and the coat condition was noted, and blood samples were taken for measurement of albumin, liver enzymes and blood clotting factors.

The between group differences for each variable were examined using analysis of variance.

Results

Figure 6B:
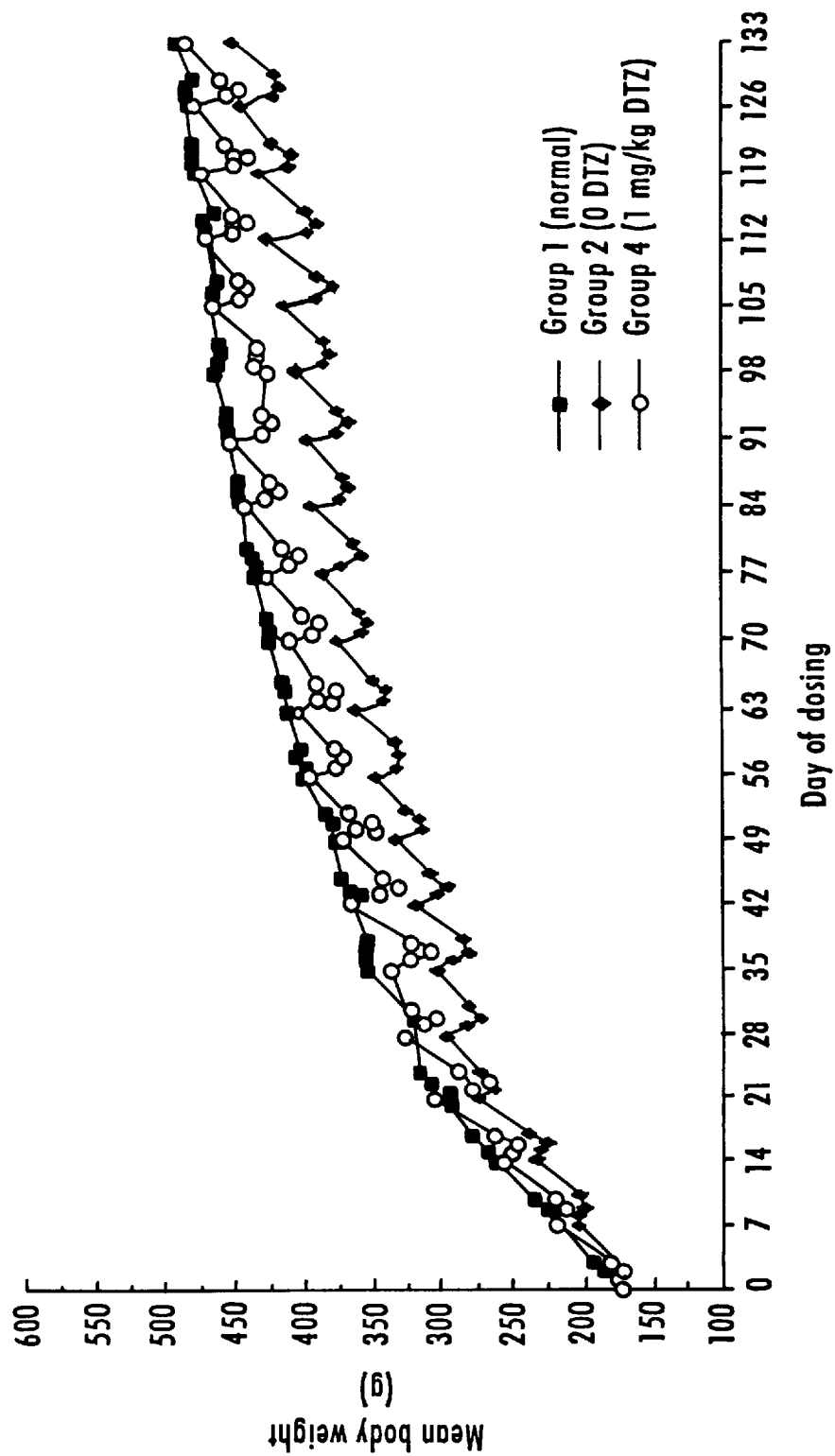
Figure 6C:
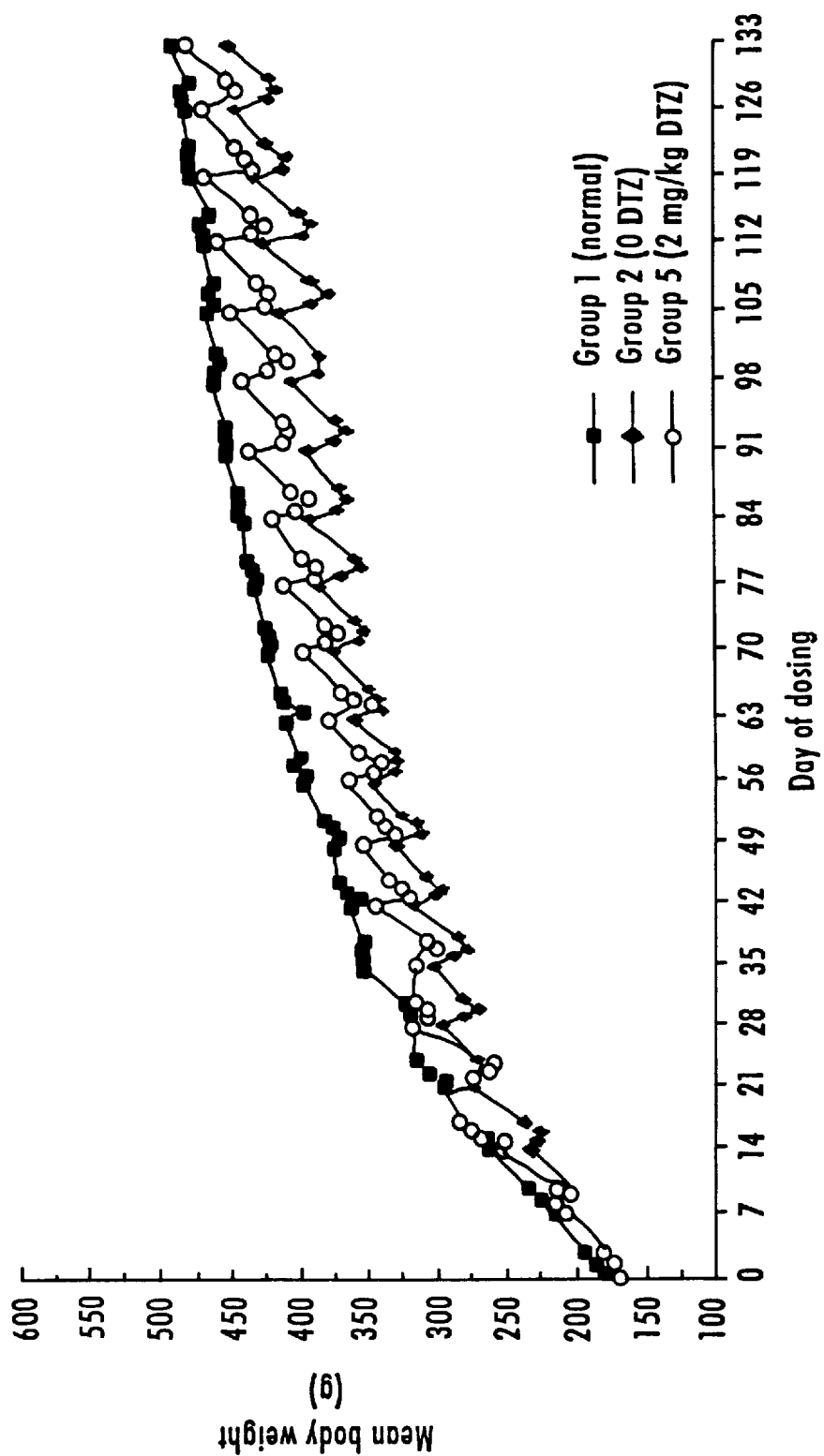

The body weight probes are shown in FIGS. 6a, b, c, which show mean rat body weight profiles during DTZ administration, and $CCl_4$ dosing for induction of cirrhosis in normal, nil DTZ and (6a) 0.5 (6b) 1.0 (6c) 2.0 mg/kg body weight. Group 1 (normal) animals progressively increased in weight from less than 200 grams to about 440 grams body weight over the study period. Group 2 (control) lost weight after each dose of $CCl_4$, and did not gain as much weight as Group 1 being 50 to 60 grams lighter at the end of the study period.

Treatment with 0.5 mg/kg/day of diltiazem (Group 2) appeared to have no significant effect of preventing $CCl_4$-induced weight loss. By contrast, in Group 3 (treated with 1.0 mg/kg/day of diltiazem), there was a transitory loss in weight after each dose of $CCl_4$.

However by the end of the study, body weights were not significantly different from normal (Group 1) but were significantly heavier than those of control animals (Group 2; $p<0.05$). The effects of 2.0 mg/kg/day (Group 5) appeared to be less than that of 1.0 mg/kg/day. Autopsy and biochemistry variables are listed in Table 3. In Groups 1 (normal) and 4 (diltiazem, 1.9 mg/kg/day) the liver and spleen appeared normal to inspection, and there was not significant ascites. By contrast Group 2 (control) showed evidence of severe liver disease. The macroscopic changes seen in the control group are supported by the reduction of plasma albumin and clotting factors and increase in plasma Canine transaminase compared with levels in the normal group of animals. Diltiazem afforded significant protection against the development of liver disease as evidenced by the protection against loss of body weight and increase in spleen size and this effect appeared to be greatest at the 1.0 mg/kg/day dose. Those primary indicators are supported by the increased protection against enzyme release. However protection against enzyme release was slightly better at the 2.0 mg/kg/day dose.

The result reported in Table 3 do, however, somewhat underestimate the protective effects of Diltiazem against liver disease as the Trial protocol means that healthy animals receive more $CCl_4$ than animals showing signs of liver disease because the weekly dose of $CCl_4$ was titrated against weight loss. The effect of this is illustrated in FIGS. 7a and 7b. FIGS. 7a and b are respectively plots of AST and ALT Enzyme release vs—Total Body load of $CCl_4$.

Discussion and Conclusion

The results of this study in rats show conclusively that low doses of diltiazem significantly prevented the development of liver disease in rats administered with $CCl_4$. Particularly significant is the observation that the greatest effect of diltiazem appeared with a dose of 1.0 mg/kg/day, in respect of body weight and spleen size (an indicator of portal vein congestions), rather than 0.5 or 2.0 mg/kg/day. The previous studies in dogs suggest that the mechanism of action is likely to be an increase in blood flow to the liver, and hence increased oxygenation of the liver. These observations in animals should now be tested in human patients with liver disease. These studies strongly suggest that it will be low doses of Diltiazem which will be effective in treating liver disease in man.

Finally, it is to be understood that various other modifications and/or alterations may be made without departing from the spirit of the present invention as outlined herein.

TABLE 3

Summary of Autopsy and biochemistry variables

|  | Group 1 (Normal) | Group 2 (0 DTZ) | Group 3 (0.5 mg/kg DTZ) | Group 4 (1 mg/kg DTZ) | Group (2 mg/kg DTZ) |
|---|---|---|---|---|---|
| Liver weight (g per kg body weight) | 34.812 ± 1.353 n = 10 | 38.695 ± 2.646 (n = 10) | 38.613 ± 2.905 (n = 5) | 40.270 ± 2.488 (n = 9) | 36.947 ± 2.115 (n = 11) |

TABLE 3-continued

Summary of Autopsy and biochemistry variables

|  | Group 1 (Normal) | Group 2 (O DTZ) | Group 3 (0.5 mg/kg DTZ) | Group 4 (1 mg/kg DTZ) | Group (2 mg/kg DTZ) |
|---|---|---|---|---|---|
| Spleen weight (g per kg body weight) | 1.560 ± 0.139 (n = 10) | 3,547 ± 0.374 (n = 10) | 3.096 ± 0.388 (n = 5) | 2.629 ± 0.515 (n = 9) | 2.460 ± 0.230 (n = 11) |
| Albumin (g/L) | 28.44 ± 0.747 (n = 9) | 25.667 ± 1.080 (n = 9) | 29.000 ± 1.484 (n = 5) | 23.875 ± 1.302 (n = 8) | 26.727 ± 0.740 (n-11) |
| ALT (U/L) | 51.780 ± 4.103 (n = 9) | 92.56 ± 15.48 (n = 9) | 140.60 ± 36.89 (n = 5) | 103.75 ± 23.15 (n = 8) | 86.55 ± 16.99 (n-11) |
| AST (U/L) | 96.89 ± 9.82 (n = 9) | 190.22 ± 43.10 (n = 9) | 177.40 ± 42.10 (n = 5) | 178.88 ± 47.10 (n = 8) | 127.55 ± 21.54 (n = 11) |
| PT-INR | 0.880 ± 0.020 (n = 5) | 0.960 ± 0.067 (n = 5) | 0.900 ± 0.000 (n-3) | 0.933 ± 0.042 (n = 6) | 0.920 ± 0.200 (n = 5) |
| APTT (secs) | 24.14 ± 4.39 (n = 5) | 25.16 ± 9.15 (n = 5) | 19.27 ± 1.77 (n-3 | 18.87 ± 1.35 (n = 6) | 28.02 ± 5.07 (n = 5) |
| Ascites | (n = 0) | (n = 2) | (n = 0) | (n = 1) | (=0) |

ALT Alanine aminotransferase versus total $CCl_4$ dose for individual rats
AST Aspartate aminotransferase versus total $CCl_4$ dose for individual rats
PT Prothrombin Time - International Normalized Ratio
APTT Activated partial thromboplastin time

EXAMPLE 4

Phase I Clinical Studies of Low-Dose Diltiazem in Patients with Liver Disease

Two studies have been commissioned to test the hypothesis that low dose diltiazem may be effective in the management of patients with chronic liver disease. As at January 1996, the first, undertaken in patients with chronic hepatitis (hepatitis C) has been completed and shows a highly significant response in two thirds of patients after just 2 weeks of treatment. This compares favorably with a 30% response rate after 12 weeks treatment with interferon. The result after diltiazem is even more significant in that all patients were refractory to treatment with interferon. A second study in patients with chronic cirrhosis of the liver is on going. However, results in the first two patients indicate that diltiazem administered as 50 mg per day in the 24 hour release formulation is increasing the hepatic clearance of antipyrine, a marker dye of hepatic function.

Study Details
a) Chronic Hepatitis

The study of the effects of low-dose diltiazem in chronic hepatitis was undertaken in 24 patients with chronic viral hepatitis (hepatitis C) who had not responded to treatment with interferon, and who had stable, but elevated blood levels of the liver enzyme alanine aminotransferase (ALT) and other enzymes. The study was undertaken at the Alfred Hospital, Melbourne, Australia and had the approval of the Ethics Review Committee at that hospital. Each patient entering the study underwent a run-in phase of two weeks followed by four periods each of two weeks. Diltiazem was administered in incremental doses of 12.5, 25, 50 and 100 mg per day in each of the two week periods. The formulation of diltiazem was Cardizem CD granules reformulated in the respective doses thereby giving low dose, but 24 hour release of the drug. Blood samples for measurement of serum ALT and other hepatic enzymes were taken twice during the run-in period, and then at the end of each incremental dose period. A final measurement of ALT was made at two weeks after completing the study.

A full report is not yet available as at January 1996, but the main results may be summarized as follows. Twenty-four patients entered the study, and 19 completed it. Five patients withdrew because of symptoms of hepatitis and social pressure unrelated to diltiazem. Reasons cited included headache, and impotence during the placebo run-in phase.

Four patients had a modest rise in ALT and two had no significant change. Thirteen had a fall in ALT which appeared to be greatest after the 50 and 100 mg doses. Six patients had a fall in ALT greater than 20%, and this appeared to be greatest after the 50 mg dose, although the response after 25 mg was almost as great. These data approximate to a halving of the evaluation of ALT after just 2 weeks of treatment.

Table 4 shows the responses in those patients who had a fall in ALT.

TABLE 4

Mean change in responders

| Time | Dose | n | Mean pre ALT level* | Mean ALT at time | P |
|---|---|---|---|---|---|
| 4 weeks | 12.5 | 13 | 147.1 | 124.8 | 0.002 |
| 6 weeks | 25 | 14 | 141.3 | 112.9 | 0.003 |
| 8 weeks | 50 | 13 | 146.3 | 109.8 | 0.001 |
| 10 weeks | 100 | 11 | 159.5 | 105.3 | 0.008 |
| post (average) |  |  | 159.6 | 123.6 | 0.003 |

*Upper limit of normal for ALT is 40 lu/ml

Data from patients who experienced more than 20% fall in ALT are shown in Table 5

| Time | Dose | n | Mean pre ALT level* | Mean ALT at time | P |
|---|---|---|---|---|---|
| 4 weeks | 12.5 | 3 | 170.3 | 126.7 | 0.002 |
| 6 weeks | 25 | 6 | 157.1 | 104.5 | 0.003 |
| 8 weeks | 50 | 6 | 142.1 | 95.6 | 0.001 |
| 10 weeks | 100 | 6 | 153.1 | 105.0 | 0.008 |
| post (average) |  | 7 | 160.0 | 106.3 | 0.003 |

The overall data are consistent with an adjunctive and therapeutic effect, and match the effects of low-dose diltiazem seen in animals. The study can not show whether a higher response rate or greater therapeutic effect may be achieved after longer periods of therapy. However, the results need to be compared with those from studies of interferon, a curative therapy, where the time to response is reported to be twelve weeks.

On this basis, the data showing incremental effects throughout the study could reflect a response to aggregate time of exposure, rather than necessary attributing the increments in effect throughout the study to the increments in dose.

It is also interesting to note that ALT did not appear to rise immediately after stopping the diltiazem. This is consistent with reoxygenation by hepatic artery dilation thereby permitting a healing effect, rather than interfering directly with the disease process. There was no evidence that 100 mg was more effective than 50 mg. The rise of enzymes in four patients indicates that the dose of the drug should be kept as low as possible.

Patients also reported that they felt better while taking the drug. Several individuals reported less tiredness and headache, and more energy.

b) Cirrhosis of the Liver

This study is logistically difficult to do and is incomplete. Ten patients with chronic but stable cirrhosis of the liver are to be recruited and each will receive 50 mg of diltiazem formulated from the 24 hour release Cardizem CD granules. An antipyrine clearance study will be performed in each patient on recruitment, after the first dose of treatment and then again after two weeks of treatment. If possible measurement of propranolol clearance will be performed at the same time. The purpose of the antipyrine clearance is to measure hepatic function in terms of the ability of the liver to excrete substances into the bile. The purpose of the propranolol clearance is to measure the capacity of the cytochrome p450 system, which is critical for oxidation and hydroxylation processes with the liver. A clearance study involves intravenous injection of a dye or marker (in this case antipyrine or radio-labelled propranolol), followed by repeated blood tests for up to 12 hours. The decay in blood levels of the marker permits measurement of the clearance rate of the dye from the body, and in this case by the liver.

As at January 1996, two patients have completed the clearance study, and both show an increase in the clearance of antipyrine. The first patient increased antipyrine clearance from 468.2 units before treatment, to 494 units after the first dose, and 730.4 units after 2 weeks treatment. This represents a 56% increase in antipyrine clearance in a patient with severe disease. The second patient with more sever disease, had a lesser but significant increase.

I claim:

1. A method for the treatment of liver disease selected from the group consisting of cirrhosis of the liver, toxic and medicamentary liver damage, a liver parenchymic disorder or hepatitis, which method comprises administering to a human or animal subject in need thereof a therapeutically active or prophylactically effective low dose amount of approximately 2.5 to 60 mg per day of a vasodilating agent which selectively increases the supply of oxygenated blood to the liver by increasing hepatic arterial inflow, wherein said vasodilating agent is selected from benzothiazepine compounds of the formula

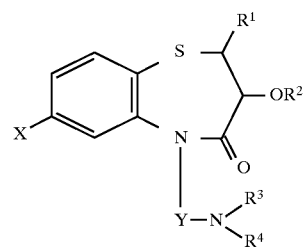

wherein $R^1$ is a phenyl group substituted or not with 1 to 3 lower alkyl groups, lower alkoxy groups or halogen atoms, $R^2$ is a hydrogen atom or a lower alkanoyl group, $R^3$ and $R^4$ are each a lower alkyl group and may be the same or different, X is a hydrogen atom or a halogen atom and Y is an alkylene group of 2 or 3 carbon atoms, or its non-toxic acid-addition salt.

2. A method in accordance with claim 1, wherein $R^1$ is 4-lower alkoxyphenyl, $R^2$ is lower alkanoyl, $R^3$ and $R^4$ are each lower alkyl, X is hydrogen and Y is ethylene.

3. A method in accordance with claim 1, wherein $R^1$ is 4-methoxyphenyl, $R^2$ is acetyl and $R^3$ and $R^4$ are each methyl.

4. A method in accordance with claim 2, wherein the benzothiazepine derivative is 3-acetoxy-5-(2-(dimethylamino-ethyl)-2,3-dihydro-2-(4-methoxyphenyl)-1,5-benzothiazepine-4-5H-one, or a non-toxic acid-addition salt thereof.

5. A method in accordance with claim 1, wherein the vasodilating agent is administered by the oral route.

6. An oral composition for the treatment of liver disease selected from the group consisting of cirrhosis of the liver, toxic and medicamentary liver damage, a liver parenchymic disorder or hepatitis, which composition comprises approximately 2.5 to 60 mg per day of a vasodilating agent, said composition being effective to selectively increase the supply of oxygenated blood flow to the liver by increasing hepatic arterial inflow, wherein said vasodilating agent is selected from benzothiazepine compounds of the formula

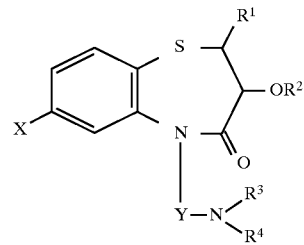

wherein $R^1$ is a phenyl group substituted or not with 1 to 3 lower alkyl groups, lower alkoxy groups or halogen atoms, $R^2$ is a hydrogen atom or a lower alkanoyl group, $R^3$ and $R^4$ are each a lower alkyl group and may be the same or different, X is a hydrogen atom or a halogen atom and Y is an alkylene group of 2 or 3 carbon atoms, or its non-toxic acid-addition salt, and in a pharmaceutically safe diluent or carrier therefor.

7. A composition in accordance with claim 6, wherein $R^1$ is 4-lower alkoxyphenyl, $R^2$ is lower alkanoyl, $R^3$ and $R^4$ are each lower alkyd, X is hydrogen and Y is ethylene.

8. A composition in accordance with claim 6, wherein $R^1$ is 4-methoxyphenyl, $R^2$ is acetyl and $R^3$ and $R^4$ are each methyl.

9. A composition in accordance with claim 7, wherein the benzothiazepine derivative is 3-acetoxy-5-(2-dimethyl amino-ethyl)-2,3-dihydro-2-(4-methyl phenyl)1,5-benzo-thiazepine-4)5H-one or a non-toxic acid-addition salt thereof.

10. A composition in accordance with claim 6 wherein the composition is in the form of a tablet, capsule, powder, suspension, emulsion or syrup.

11. A composition in accordance with claim 6 wherein the composition is in unit dosage solid form and wherein the vasodilating agent is present in an amount of from about 5 to about 95% by weight and the remainder comprising conventional pharmaceutical carrier(s).

12. A composition in accordance with claim 6 in the form of an aqueous solution.

13. A composition in accordance with claim 6 in the form of a sustained release composition.

* * * * *